US006911435B1

(12) United States Patent
Cohn et al.

(10) Patent No.: US 6,911,435 B1
(45) Date of Patent: Jun. 28, 2005

(54) METHOD OF TREATING LEUKOPENIA WITH ADENOSINE

(75) Inventors: Ilan Cohn, Herzlia (IL); Pnina Fishman, Herzlia (IL)

(73) Assignee: Can-Fite Biopharma Ltd., Petach Tikva (IL)

(*) Notice: Subject to any disclaimer, the term of this patent is extended or adjusted under 35 U.S.C. 154(b) by 0 days.

(21) Appl. No.: 09/462,202

(22) PCT Filed: Jul. 10, 1998

(86) PCT No.: PCT/IL98/00324
§ 371 (c)(1),
(2), (4) Date: Jan. 4, 2000

(87) PCT Pub. No.: WO99/02143
PCT Pub. Date: Jan. 21, 1999

(30) Foreign Application Priority Data

Jul. 10, 1997 (IL) .................................. 121272

(51) Int. Cl.$^7$ .............................................. A61K 31/70
(52) U.S. Cl. ......................................................... 514/46
(58) Field of Search ............................ 514/46, 47, 79; 536/26.7, 27.6–27.63; 558/75

(56) References Cited

U.S. PATENT DOCUMENTS

| 4,364,922 A | * | 12/1982 | Berne et al. ................... 514/46 |
| 4,673,563 A | * | 6/1987 | Berne et al. ................... 514/46 |
| 5,104,859 A | * | 4/1992 | Sollevi ........................... 514/46 |
| 5,145,771 A | * | 9/1992 | Lemasters et al. ............. 435/1 |
| 5,231,086 A | * | 7/1993 | Sollevi ........................... 514/46 |
| 5,449,665 A | * | 9/1995 | Sollevi ........................... 514/46 |
| 5,534,504 A | * | 7/1996 | Sollevi ........................... 514/46 |
| 5,648,341 A | * | 7/1997 | Sollevi ........................... 514/46 |
| 5,677,290 A | * | 10/1997 | Fukunaga ....................... 514/46 |
| 5,679,650 A | * | 10/1997 | Fukunaga et al. ............. 514/46 |
| 5,686,114 A | * | 11/1997 | Welsh ........................... 424/601 |
| 5,731,296 A | * | 3/1998 | Sollevi ........................... 514/46 |
| 5,882,927 A | * | 3/1999 | Bennett et al. ............. 435/375 |
| 5,958,907 A | * | 9/1999 | Welsh ........................... 514/108 |
| 2001/0031742 A1 | * | 10/2001 | Fishman et al. ............. 514/45 |
| 2002/0037871 A1 | * | 3/2002 | Fishman et al. ............. 514/46 |

FOREIGN PATENT DOCUMENTS

| EP | 0066918 | * | 12/1982 |
| GB | 797237 | * | 7/1958 |
| WO | WO 94/17809 A1 | * | 8/1994 |
| WO | WO 00/10760 | | 3/2000 |
| WO | WO 00/40251 A1 | * | 7/2000 |
| WO | WO 01/19360 A2 | * | 3/2001 |
| WO | WO 02/09701 A1 | * | 7/2002 |

OTHER PUBLICATIONS

Drury et al., "The Physiological Activity of Adenine Compounds with Especial Reference to their Action Upon the Mammalian Heart," *Journal of Physiology* (Cambrige), 68, 213–237 (1929).*

Sollevi (VII), "Cardiovascular Effects of Adenosine in Man; Possible Clinical Implications," *Progress in Neurobiology,* 27, 319–349 (1986).*

Homeister et al., "Combined Adenosine and Lidocaine Administration Limits Myocardial Reperfusion Injury," *Circulation,* 82(2), 595–608 (Aug., 1990).*

Newberg et al., "Cerebral and Systemic Effects of Hypotension Induced by Adenosine or ATP in Dogs," *Anesthesiology,* 62(4), 429–436 (Apr., 1985).*

Berkow et al. (eds.), *The Merck Manual of Diagnosis and Therapy,* 16th Edition, Merck & Co., Rahway, NJ, May, 1992, only pp. 1225–1243 supplied.*

Calabresi et al., "Antineoplastic Agents," Ch. 52 in *Goodman and Gilman's The Pharmacological Basis of Therapeutics, Eighth Edition,* Gilman et al. (eds.), Pergamon Press, 1990, New York, NY, only pp. 1209 & 1215–1219 supplied.*

Rall, "Drugs Used in the Treatment of Asthma," Ch. 25 in *Goodman and Gilman's The Pharmacological Basis of Therapeutics, Eighth Edition,* Gilman et al. (eds.), Pergamon Press, 1990, New York, NY, only pp. 618 & 624–625 supplied.*

Boyd et al., "The Neutralization of Aminopterin–Induced Leukopenia by Adenosine–5–phosphoric Acid," *Journal of Laboratory and Clinical Medicine,* 41, 931–935 (1953); *Chemical Abstracts,* 47(19), Abstract No. 10116c–e (Oct. 10, 1953); CAPlus cite is "1953: 59519."*

Matsumoto et al., "Nucleoside–Nucleotide Mixture Increases Peripheral Neutrophils in Cyclophosphoramide–Induced Neutropenic Mice," *Nutrition,* 11(3), 296–299 (May/Jun., 1995); *Chemical Abstracts,* 123(19), pages 1043–1044, Abtract No. 255501q (Nov. 6, 1995).*

Lejnieks et al., "Granulocyte Colony–Stimulation Factor Expression from Transduced Vascular Smooth Muscle Cells Provides Sustained Neutrophil Increases in Rats," *Human Gene Therapy,* 7, 1431–1436 (Aug. 1, 1996).*

Thiel et al., "Effects of Adenosine on the Functions of Circulating Polymorphonuclear Leukocytes during Hyperdynamic Endotoxemia," *Infection and Immunity,* 65(6), 2136–2144 (Jun., 1997).

Roy et al., "A Single Amino Acid Difference within the Folate Transporter Encoded by the Murine RFC–1 Gene Selectively Alters its Interaction with Folate Analogues," *Journal of Biological Chemistry,* 273(5), 2526–2531 (Jan. 30, 1998).

(Continued)

Primary Examiner—James O. Wilson
Assistant Examiner—Lawrence Crane
(74) Attorney, Agent, or Firm—Browdy and Neimark, P.L.L.C.

(57) ABSTRACT

Adenosine and active agent which interact with the adenosine system are used to treat conditions of weakened, immune system, as an anti-cancer therapy and for improving the therapeutic index of a variety of therapeutic drugs.

15 Claims, 5 Drawing Sheets

OTHER PUBLICATIONS

Matherly et al., "Enhanced Polyglutamylation of Aminopterin Relative to Methotrexate in the Ehrlich Ascites Tumor Cell in Vitro," *Cancer Research*, 45, 1073–1078 (Mar., 1985).

Marshall et al., "General Anesthetics," Ch. 14 in *Goodman and Gilman's The Pharmacological Basis of Therapeutics, Eighth Edition*, Gilman et al. (eds.), Pergamon Press, 1990, New York, NY, only pp. 298–300 supplied (see p. 300, col. 1, for vitamin B–12–related side effects of Nitrous Oxide).

Fukunaga et al. (II), "Hypotensive Effects of Adenosine and Adenosine Triphosphate Compared with Sodium Nitroprusside," *Anesthesia and Analgesia*, 61(3), 273–278 (Mar., 1982).

Hirano et al., "Functional Coupling of Adenosine $A_{2a}$ Receptor Inhibiton of the Mitogen–Activated Protein Kinase Cascade in Chinese Hamster Ovary Cells," *Biochemical Journal*, 316(Pt. 1), 81–86 (May 15, 1996).

M.G. Collis, The Vasodilator Role of Adenosine, Pharmacology & Therapeutics, vol. 41, No. 1/2, The Journal of The International Encyclopedia of Pharmacology and Therapeutics, 1989, pp. 143–162, Month of publication could not be determined from copy supplied.

I. Barasoain et al., Isoprinosine Restores in Vitro T Lymphocyte Functions of Cyclophosphamide Immunosuppressed Mice, Int. J. Immunopharmac., vol. 9, No. 4, 1987, XP002083810, pp–489–496, Month of publication data is unavailable for this reference.

J.E.F. Reynolds, Ed. –The Martindale Extra Pharcamocopoeia, $31^{st}$ Edition, 1996–Royal Pharmaceutical Society, London XP002083816, pp. 813–814,Month of publication data is unavailable for this reference.

J. Epstein et al., Protection of normal Hematopoietic Stem Cells from the Toxicity of Purine Base Analogs: In Vivo Application, Cancer Treatment Reports, vol. 68, No. 9, 1984, XP002083811, pp. 1153–1156, Month of publication data is unavailable for this reference.

R.C. Jackson et al., Biochemical Approaches to Enhancement of Antitumor Drug Selectivity: Selective Protection of Cells from 6–Thioguanine and 6–Mercaptopurine by Adenosine—Cancer Treatment Reports, vol. 64, No. 12, 1980, XP002083812, pp. 1347–1353 Dec., 1980).

M. Debatisse et al., The Control of Cell Proliferation by Preformed Purines: A Genetic Study. II. Pleiotropic Manifestations and Mechanism of a Control Exerted by Adenylic Purines on PRPP Synthesis, Somatic Cell Genetics, vol. 3, No. 5, 1997, XP002083813, pp. 513–527, Month of publication data is unavailable for this reference.

P. Gentile et al., Approaches to Ablating the Myelotoxicity of Chemotherapy, CRC Critical Reviews in Oncology/Hematology, vol. 7, 1987, XP002083814, pp. 73–75, Month of publication data is unavailable for this reference.

Y.–X. Feng et al., Suppressive effects of adenosine on nonspecific and humoral immunities in mice, Dialog (R) File 73: Embase, Accession No. 9340892: ACTA Pharmacol. Sin., vol. 15, No. 5, 1994, XP002083815, pp. 473–476, Month of publication data is unavailable for this reference.

M. Iigo et al., Relationship between Antitumor Effect and Metabolites of 5–Fluorouracil in Combination Treatment with 5–Fluorouracil and Guanosine in Ascites Sarcoma 180 Tumor System, Cancer Res., vol. 43, No. 12, Pt. 1, 1983, XP002102063, pp. 5687–5694 (Dec., 1983).

E. Rapaport, Experimental Cancer Therapy in Mice by Adenine Nucleotides, Eur. J. Cancer Clin. Oncol., vol. 24, No. 9, 1988, XP002102064, pp. 1491–1497, Month of publication data is unavailable for this reference.

H.B. Tey et al.,Adenosine Modulates Cell Growth in Human Epidermoid Carcinoma (A431) Cells, Biochem. Biophys. Res. Commun., vol. 187, No. 3, 1992, XP002102065, pp. 1486–1492 (Sep. 30, 1992).

Q. Wang et al., Antineoplastic action of adenosine triphosphate, Dialog (R) File 159: Cancerlit (C): Accession No. 01001704: Chung Hua I Hsueh Tsa Chih, vol. 73, No. 7, 1993, XP002102066, pp. 434–436, Month of publication data is unavailable for this reference.

E. Rapaport et al., Anticancer activites of adenine nucleotides in mice are mediated through expansion of erythrocyte ATP pools, Proc. Natl. Acad. Sci., USA, vol. 86, 1989, XP002102067, pp. 1662–1666 (Mar., 1989).

G.B. Grindey et al., Antitumor Activity of N6–Phenyladenosine, an Inhibitor of Adenosine Utilization, in Combination with Related Purine Analogs, Cancer Res., vol. 33, 1973, XP002102068, pp. 2459–2463 (Oct., 1973).

M. Tezuka et al., Potentiation of the Antitumor Effects of 5–Fluorouracil by Some Nucleotides, and their Possible Role in the Potentiation, JPN. J. .Exp. Med., vol. 53, No. 3, 1983, XP002102069, pp/ 155–163, Month of publication data is unavailable for this reference.

S. Bajaj et al., Adenosine and Adenosine Analogues are More Toxic to Chronic Lymphocytic Leukemia Than to Normal Lymphocytes, Blood, vol. 62, 1983, XP002102070, pp. 75–80. (Jul., 1983).

T. Hidaka et al., Eff4ects of a New Adenosine Deaminase Inhibitor, Isocoformycin, on Toxicity, Antitumor Activity and Tissue Distribution of Formycin A and 9–Beta–D–Arabinofuranosyladenine, J. Antibiot., vol. 33, No. 3, 1980, XP002102071, pp. 303–309 (Mar., 1980).

H. Tanaka et al., Potentiation of Cytotoxicity and Antitumor Activity of Adenosine Analogs by the Adenosine Deaminase Inhibitor Adecypenol, J. Antibiot., vol. 42, No. 11, 1989, XP002102072, pp. 1722–1724 (Nov., 1989).

A.K. Ghose et al., Structural mimicry of adenosine by the antitumor agents 4–methoxy– and 4–amino–8–(beta–D–ribofuranosy amino)pyrim ido[5,4–d] pyrimidine as viewed by a molecular modeling method, Proc. Natl. Acad. Sci. USA, Vo. 86, 1989, XP002102073, pp. 8242–8246 (Nov., 1989).

R.E. Klabunde, Dipyridamole Inhibition of Adenosine Metabolism in Human Blood, European Journal of Pharmacology, vol. 93, 1983, pp. 21–26, Month of publication data is unavailable for this reference.

P. Paul et al., Modulation of erythropoietin production by adenosine, J. Lab. Clin. Med. 1988, vol. 112, No. 2, pp. 168–173 (Aug. 1988).

Eigler et al., Endogenous Adenosine Curtails Lipopolysaccharide–Stimulated Tumour Necrosis Factor Synthesis, Scandinavian Journal of Immunology, vol. 45, 1997, pp. 132–139, Month of publication data is unavailable for this reference.

M.G. Bouma et al., Differential Regulatory Effects of Adenosine on Cytokine Release by Activated Human Monocytes, The Journal of Immunology, 1994, pp. 4159–4168, Month of publication data is unavailable for this reference.

M. Pospisil et al., Elevation of Extracellular Adenosine Induces Radioprotective Effects in Mice, Radiation Research, vol. 134, 1993, pp. 323–330, Month of publication data is unavailable for this reference.

G.A. Weisman, Cellular Responses to External ATP Which Precede an Increase in Nucleotide Permeability in Transformed Cells, Journal of Cellular Physiology, vol. 119, 1984, pp. 211–219, Month of publication data is unavailable for this reference.

Heppel et al., Permeabilization of Transformed Cells in Culture by External ATP, The Journal of Membrane Biol., vol. 86, 1985, pp. 189–196, Month of publication data is unavailable for this reference.

A. Surprenant et al., The Cytolytic $P_{2z}$ Receptor for Extracellular ATP Identified as a $P_{2x}$ Receptor ($P2x_7$), Science, vol. 272, 1996, pp. 735–738 (May 3, 1996).

J.W. Daly, Adenosine Receptors: Targets for Future Drugs, Journal of Medicinal Chemistry, vol. 25, No. 3, 1982, pp. 197–207 (Mar., 1982).

R.M. Berne, The Role of Adenosine in the Regulation of Coronary Blood Flow, Circulation Research, vol. 47, No. 6, 1980, pp. 807–813 (Dec., 1980).

J.G. Dobson, Jr., Mechanism of Adenosine Inhibition of Catecholamine–Induced Responses in Heart, Circulation Research, vol. 52, No. 2, 1983, pp. 151–160. (Feb., 1983).

U. Soderback et al., Anti–aggregatory effects of physiological concentrations of adenosine inhuman whole blood as assessed by filtragometry, Clinical Science, vol. 81, 1991, pp. 691–694, Month of publication data is unavailable for this reference.

M. Pines, Inhibition of the Proliferation of Nb2 Cells by Femtomolar Concentrations of Cholera Toxin and Partial Reversal of the Effect by 12–0–Tetradecanoyl–Phorbol–13–Acetate, Journal of Cellular Biochemistry, vol. 37, 1988, pp. 119–129, Month of publication data is unavailable for this reference.

* cited by examiner

METHOD OF TREATING LEUKOPENIA WITH ADENOSINE

RELATED APPLICATIONS

This is a National Phase Application of PCT/IL9/00324 filed Jul. 10, 1998, which is based on Israeli Application 121272 filed Jul. 10, 1997, the subject matter of both being incorporated herein by reference.

FIELD OF THE INVENTION

The present invention concerns drugs for use in human therapy. More specifically, the present invention concerns pharmaceutical uses of adenosine as well as agents that interact with the adenosine system.

PRIOR ART

The following is a list of prior art references considered to be relevant as background to the invention:
1. Daly, J. W., Adenosine receptors: Targets for future drugs. *J. Med. Chem.*, 25:197–207, 1982.
2. Stiles, G. L., Adenosine receptors and beyond: Molecular mechanisms of physiological regulation, *Clin. Res.*, 38:10–18, 1990.
3. Collis, M. G., The vasodilator role of adenosine, *Pharmacol. Ther.*, 41:143–162, 1989.
4. Klabunde, R. E., Dipyridamole inhibition of adenosine metabolism in human blood, *European J. Pharmacol.*, 93:21–26, 1983.
5. Berne, R. M., The Role of adenosine in the regulation of coronary blood flow, *Circ. Res.*, 47:807, 1980.
6. Dobson, J. G., Jr., Mechanism of adenosine inhibition of catechol-amine-induced responses in heart, *Circ. Res.*, 52:151, 1983.
7. Soderback, U., Sollevi, A., Wallen, V. H. Larsson, P. T., and Hjemdahl, P., Anti-aggregatory effects of physiological concentrations of adenosine in human whole blood as assessed by filtragometry, *Clin. Sci.*, 81:691–694, 1991.
8. Paul, P., Rothmann, S. A., and Meagher, R. C., Modulation of erythropoietin production by adenosine, *J. Lab. Clin. Med.*, 112:168–173, 1988.
9. Elgler, A., Greten, T. F., Sinha, B., Haslberger, C., Sullivan, G. W. and Endres, S., Endogenous adenosine curtails lipopolysaccharide-stimulated tumor necrosis factor synthesis, *Scand. J. Immunol.*, 45:132–139, 1997.
10. Bouma, M. G., Stad, R. D., van den Wildenberg, F. A. J. M., and Buurman, W. A., Differential regulatory effects of adenosine on cytokine release by activated human monocytes, *The J. of Immunol.*, 153:4159–4168, 1994.
11. Pospisil, M., Hofer, M., Netikova, J., Pipalova, I., Vacek, A., Bartonickova, A., and Volenec, K., Elevation of extracellular adenosine induces radioprotective effects in mice., *Radiation Research*, 134:323–330, 1993.
12. Bajaj, S., Insel, J., Quagliata, F., Hirschhorn, R. and Silber. R., Adenosine and adenosine analogues are more toxic to chronic lymphocytic leukemia than to normal lymphocytes, *Blood*, 62:75–80, 1983.
13. Tey, H. B., Khoo, H. E., and Tan, C. H., adenosine modulates cell growth in human epidermoid carcinoma (A431) cells, *Biochem & Biophysci. Res. Communications.*, 187:1486–1492, 1992.
14. Rapaport, E., Experimental cancer therapy in mice by adenine nucleotides, *Eur. J. Cancer Oncol.*, 24:1491–1497, 1988.
15. Rapaport, E., J. Fontaine, Anticancer activities of adenine nucleotides in mice are mediated through expansion of erytrocyte ATP pools, *Proc. Natl. Acad. Sci.*, 86:1662–1666, 1989.
16. Weisman, G. A., De, B. K., Pritchard, R. S., and Heppel, L. A., Cellular responses to external ATP which precede an increase in nucleotide permeability in transformed cells, *J. of Cellular. Physiol.*, 119:211–219, 1984.
17. Heppel, L. A., Weisman, G. A., Friedberg, I., Permeabilization of transformed cells in culture by external ATP., *Membrane Biology*, 86:189–196, 1985.
18. Surprenant, A., Rassendren, F., Kawashima, E., North, R. A. and Buell, G., The cytolytic $P_{2z}$ receptor for extracellular ATP identified as a $P_{3x}$ receptor ($P2X_7$), *Science*, 272:735–738, 1996.
19. Jackson, R. C., Ross, D. A., Harkrader, R. J., Epstein, J., Biochemical approaches to enhancement of antitumor drug selectivity: selective protection of cells from 6-thioguanine and 6-mercaptopurine by adenosine, *Cancer Treatment Reports*, 64:1347–1353, 1980.
20. Gentile, P., Epremian B. E., Approaches to ablating the myelotoxicity of chemotherapy. CRC Critical Reviews in Oncology/Hematology 7:71–87, 1987.
21. Epstein, J., Preisler, H. D., Protection of normal hematopoietic stem cells from the toxicity of purine base analogs: in vivo application. *Cancer Treatment Reports*, 68:1153–1156, 1984.
22. Pines, M., Ashkenazi, A., Cohen-Shapnik, N, Binder, L. and Gertler, A., Inhibition of the proliferation of Nb2 cells by femtomolar concentrations of cholera toxin and partial reversal of the effects by 12-0-tetradecanoyl-phorbol-13-acetate, *J. of Cellular Biochem.*, 37:119–129, 1988.

The acknowledgement of these references herein will be made by indicating their number from the above list, within brackets.

BACKGROUND OF THE INVENTION

Adenosine is a purine nucleoside which is known to act extracellularly to regulate different physiological processes through its binding to specific cell surface receptors (A1 and A2 receptors)[1,2,3]. The fact that adenosine exerts an extracellular effect was demonstrated, for example, by an increased effect of adenosine on cells when given together with dipyridamole, which inhibits uptake of adenosine by cells[4].

Adenosine has been known to affect the cardiac rhythm and accordingly has been clinically used to protect the myocardium in various pathological situations[5,6]. In addition, adenosine is also known as having both vasoconstrictor effect on the kidney and a vasodilator effect in other vascular beds. Adenosine is also known to have an effect on blood cells including: inhibition of platelet aggregation[7]; stimulation of red blood cell hematopoiesis through the production of erythropoietin; exerting an anti-inflammatory effect manifested by inhibition of inflammatory cytokines[9,10]; and reduction of septic shock. Adenosine was also shown to have a radioprotective effect when administered for a few minutes (about 15 mins) prior to the radiotherapeutic treatment[11].

Adenosine was also known to exert an anti-proliferative effect on cancer cells. Bajaj et al., 1983[12] noted that adenosine and adenosine analogs have a toxic effect on lymphocytic leukemia cells, which was more pronounced than the toxic effect on normal lymphocytes. Furthermore, Tey et al., 1992[13] showed that adenosine had an effect in modulating cell growth in human epidermoid carcinoma cells. In addition, it has been noted in the literature[14] that parenterally administered adenine nucleotides (AMP, ADP and ATP) inhibit tumor development in mice[15]. ATP has been reported to increase Permeabilization of transformed cells[16,17], but it should be noted that ATP exerts its effect through the cellular receptors, P2X, P2Y and P2Z[18], which are different than that the A1 and A2 receptors through which adenosine exerts its regulatory effect.

White blood cells (leukocytes) consist of three basic groups of cells: granulocytes, monocytes and lymphocytes. Many therapeutic drug treatments have undesired side effects manifested in reduction of leukocytes, and particularly reduction in the count and relative proportion of granulocytes (which are typically 70% of the white blood cells), and particularly of neutrophils, which typically constitute more than about 90% out of the granulocytes. Examples of drugs which cause reduction in count of leukocytes, and particularly neutrophils, are cytotoxic drugs, e.g. such used in cancer chemotherapy, neuroleptic drugs, and others. The effect of reduction in white blood cell count is usually referred to in the art as "leukopenia" and reduction in the count of neutrophils as "neutropenia". One major adverse effect of leukopenia, and particularly of neutropenia, is an increase in susceptibility of individuals to opportunistic infectious diseases. In many cases, particularly in cancer chemotherapy, the patients very often die from such opportunistic infectious diseases (e.g. from lung infection) and not from their primary disease, i.e. cancer. Drugs which can protect or inhibit the undesired toxic side effect of leukopenia, and particularly of neutropenia, would thus be highly desirable. Jackson et. al.[19] reviewed by Gentile et al.[20], showed that the toxic effect of two purine analogs (6-thioguanine and 6-mercaptopurine) on lymphoblaste and fibroblasts can be inhibited by adenosine. It was postulated that this effect is in view of the adenoine's inhibition of production of phosphoribosylpyrophosphate (PRPP). Jackson et al. point in the conclusion of their study to the possibility of developing cytotoxic drugs with a higher selectivity towards cancer cells, based on different enzyme patterns between tumor and normal cells. It should be noted that the work of Jackson et al. was conducted in vitro only, and when adenosine was tried in vivo, it was shown by Epstein et al.[21] that in vivo protection towards toxic effect of purine analog can be achieved with adenosine levels of about 500 mg/kg body weight. It should, however, be noted that at such mega doses, adenosine would likely be toxic and have a variety of side effects by itself.

GENERAL DESCRIPTION OF THE INVENTION

The present invention concerns a novel use of adenosine and various agents, including other nucleosides, nucleoside derivatives, and agents that interact with the adenosine system, that include: agonists and antagonists of adenosine receptors, inhibitors or blockers of adenosine transporters, as well as inhibitors of enzymes involved in adenosine metabolism, e.g. adenosine kinase inhibitor and adenosine diaminase inhibitor.

In accordance with the present invention it was found that adenosine has an effect in inducing proliferation of bone marrow cells, resulting in increase in the number of leukocytes and particularly of neutrophils in the peripheral blood. It was furthermore found in accordance with the invention that adenosine has a protective effect against some toxic effect of chemotherapeutic drugs, particularly protection against reduction in count of leukocytes, particularly neutrophils, which is otherwise caused by the chemotherapeutic drug. In addition, it was found in accordance with the invention that adenosine potentiates the specific anti-tumor activity of chemotherapeutic drugs. Still further, it was found in accordance with the invention, that certain of the adenosine activities noted above can be modulated by various agents that interact with the adenosine system.

In in vivo studies in experimental animal it was shown that the overall effect of adenosine when administered together with a chemotherapeutic drug is to increase the therapeutic index, namely, reducing toxic side effects and improving specific activity. In the following, the term "increase in therapeutic index" will be used to denote either improvement in the therapeutic effect of a drug, namely increasing its efficacy on a specific target cell, or reducing non desired toxic side effects manifested on cells other than the target cells, or both.

In the following, the term "target cells" will be used to denote the target of said drug; the term "non-target cells" will be used to denote cells other than target cells on which the drug reserves a cytotoxic side effect.

The term "anti-cancer chemotherapeutic drug" will be used to denote a cytotoxic drug or a cocktail comprising a combination of two or more cytotoxic drugs given to an individual for the purpose of reducing the patient's tumor mass.

The term "agents that interact with the adenosine system" used above and which may be used further below, means to denote a variety of agents which interact with receptors, transporters or enzymes which regulate or mediate the adenosine interaction with cells. As known, extracellular adenosine can bind to a number of receptors on the cell membrane including, among others, the A1 and the A2 receptors. Furthermore, cell membranes typically contain nucleoside transporters which can transport adenosine (as well as other nucleosides) into and out of the cell. Furthermore, in the extracellular medium surrounding the cells, as well as within the cells, there are various enzymes which can metabolize adenosine. The effect of extracellularly applied adenosine on cells is a combination of these three different mechanisms, (namely binding to receptors, transport through nucleoside transporters and breakdown by enzymes). It was found in accordance with the invention that adenosine exerts its differential effect on bone marrow cells on the one hand and cancer cells on the other hand, through interaction via these mechanisms (different ones in each case) and use of agents which interact through these mechanisms may thus have similar effects to that of adenosine or an effect in modulating the adenosine activity. Agents that interact with the adenosine system include receptor agonists and antagonists, adenosine diaminase or adenosine kinase inhibitors, transport inhibitors, etc. In addition, as will no doubt be appreciated by the artisan, although the use of adenosine is preferred in accordance with the invention, other nucleosides, as well as nucleoside derivatives, may potentially be used to obtain qualitatively similar effects to that of adenosine. In the following, the invention will be described at times with particular reference to adenosine, it being understood that the invention is not limited thereto but rather applies also to all the other active ingredients mentioned above.

In addition, as will be explained further below, the invention has several different aspects. One aspect is concerned with the induction of proliferation of bone marrow cells. Another aspect is concerned with inhibition of proliferation of tumor cells. A third aspect is concerned with the increased efficacy of some drugs, notably chemotherapeutic drugs, on target cells, particularly cancer cells. A fourth aspect is concerned with increasing therapeutic index of certain drugs, notably chemotherapeutic and neuroleptic drugs, by either increasing their specific effect on the target cell, by reducing their toxic side effects in reducing blood leukocyte count, or both. While adenosine is useful, and indeed the preferred active agent in all such aspects of the invention, other active ingredients which may be contemplated in accordance with the invention may not be readily utilized in all aspects of the invention and may thus be chosen for use in connection with one or more specific aspects only. For example, an adenosine receptor antagonist may be used in the bone marrow proliferation inducing aspect of the invention, as it was found to have such an activity. Against this, the adenosine receptor antagonist was found to have an effect in neutralizing adenosine's inhibitory effect on proliferation of tumor cells, and accordingly may not be used in the tumor proliferation inhibition aspect of the invention.

Active ingredients other than adenosine for use in each of the invention's therapeutic aspects, may be chosen based on simple screening using in vitro proliferation assays.

Many drugs have cytotoxic side effects on a variety of cells, particularly metabolically active and dividing cells. These include hematopoietic cells such as bone marrow cells, leukocytes, particularly neutrophils, as well as fibroblasts, cells of the digestive tract, and others. In the following, a reduction in leukocyte count or neutrophil count by cytotoxic drugs, will be referred to herein, at times, as "drug-induced leukopenia" or "drug-induced neutropenia", respectively.

In the following, whenever mention is made to "leukopenia", it should be understood as referring particularly to "neutropenia" (drug-induced leukopenia is primarily manifested in reduction in the level of neutrophils).

Adenosine and some other of said active ingredients may be used in accordance with one aspect of the invention for inducing proliferation of bone marrow cells. This aspect of the invention is applicable in a variety of clinical situations, For example, adenosine and the other of said active ingredients may be used for treatment of patients having a disease or disorder caused by or associated with weakening of the immune system, e.g. in the case of inherited or acquired immune deficiency. Also certain autoimmune diseases are associated with an overall weakening of the immune system and said active ingredients may be used then as well. Another situation of a weakened immune system which may be treated in accordance with this aspect of the invention, is such which often occurs in advanced stages of cancer. This aspect of the invention is also useful in therapy in the case of leukopenia and particularly neutropenia occurring as a result of chemotherapeutic drug or neuroleptic drug administration. The effect of adenosine or the other of said active ingredients in countering drug-induced leukopenia, can be manifested by more limited reduction in the amount (or count) of the leukocytes, as compared to the count without adenosine, or at times even an increase in the amount of the cells, even to levels above control.

In accordance with an additional aspect of the invention, adenosine, and some of said active ingredients, are used to inhibit proliferation of tumor cells, within the framework of anti-cancer therapy.

Furthermore, in accordance with another aspect of the invention, adenosine and some of said active ingredients may also be used to increase efficacy of cytotoxic drugs towards certain target cells, particularly of anti-cancer chemotherapeutic drugs towards cancer cells. This increase in efficacy can be manifested by a more pronounced destruction of tumor cells at a given dose of the drug, or reduction in the required dose of the drug needed to achieve a certain therapeutic effect By a further of its aspects, adenosine as well as some of said active ingredients other than adenosine, are used for improving the therapeutic index of certain therapeutic drugs, particularly improving the ratio between a specific therapeutic effect of the chemotherapeutic drug or neuroleptic drug on its respective target cell versus toxic side effects of these drugs manifested by leukopenia. In other words, the adenosine or some of the active ingredients other than the adenosine may give rise either to an increase in efficacy of a drug which may mean the ability to use a lower dose, to shorten the treatment period, etc., may give rise to reduction of the aforementioned toxic side effect, or both. The active ingredient in accordance with this aspect may be administered in combination with the therapeutic drug, e.g. may be included together in one pharmaceutical composition with said therapeutic drug.

The present invention provides, for each of the above-mentioned aspects, a method of therapeutic treatment comprising administering an effective amount of the respective active ingredient to an individual in need. Still further provided for each of the aspects of the invention, is the use of the active ingredient for the purpose of preparing a pharmaceutical composition for the therapeutic treatments of diseases or conditions which are within the scope of the invention's various aspects, noted above. Furthermore, for each of these aspects, the present invention provides a pharmaceutical composition for use in the treatment of a variety of conditions, diseases or disorders, which are within the scope of the above aspects, the composition comprising an effective amount of said active ingredient.

The term "effective amount" used above and below should be understood as meaning an amount of adenosine or another of said active ingredients other than adenosine which is capable of achieving a desired therapeutic effect. The desired therapeutic effect depends on the type and mode of treatment When, for example, said active ingredient is administered to counter drug-induced leukopenia, an effective amount of the active ingredient may be an amount which protects the individual against the drug-induced reduction in the count of leukocytes, particularly neutrophils; an amount of the active ingredient which can give rise to an increase in an already decreased level of such cells, e.g. restore the level to a normal level or sometimes even above; etc. Where the active ingredient is administered in order to potentiate the effect of an anti-cancer chemotherapeutic drug, an effective amount may be an amount which either increases the cancer specific toxicity of the chemotherapeutic treatment; an amount which is effective in reducing the amount of the chemotherapeutic drug or drug combination required to achieve a desired effect of the chemotherapeutic drug or drug combination, i.e. reduction of the tumor load; etc. An example of an effective amount is a daily administration of adenosine of above about 10 µg./kg body weight, preferably at least about 25 µg/Kg body weight; and below about 50 mg/Kg body weight, preferably below about 10 mg/Kg body weight and most preferably below about 1 mg/Kg body weight. Typically, the amount of adenosine administered will be within the range of 30–100 µg/kg body weight. Such an amount of adenosine is typically administered in a single daily dose although at times a daily dose may be divided into several doses administered throughout the day or at times several daily doses may be combined into a single dose to be given to the patient once every several days, particularly if administered in a sustained release formulation.

By one embodiment of the invention, the composition, particularly where the active ingredient is adenosine, is an oral composition. Such a composition may be provided as a liquid, e.g. a syrup; it may be provided as powder or lyophilisate for mixing with a palatable liquid prior to administration; it may be provided in a dosage form, e.g. in the form of a capsule or a pill, etc.

By another embodiment, the composition is formulated for parenteral administration (intravenous, intramuscular, subcutaneous or intraperitoneal administration). A composition in accordance with this embodiment, may be provided as a liquid mixture ready for use, or may also be provided as a powder or lyophilisate for mixing with saline or any other physiological liquid prior to use.

In accordance with a further embodiment, the adenosine composition is provided as an inhalable composition in the form of a spray or aerosol.

In accordance with a still further embodiment, the composition is provided in the form of a patch for transdermal administration.

In the case of the aspects of the invention concerned with reducing toxic side effects or increasing therapeutic index of therapeutic drugs, the administration of said active ingredient may begin a period of time, several days, prior to treatment with the therapeutic drug, e.g. the chemotherapeutic drug or a neuroleptic drug, and may then be continued also throughout the period of administration of the drug. Such prior administration may provide an extra protective effect, for example against the drug-induced leukopenia At times a pre-treatment with said active ingredient may be sufficient, and at other times said active ingredient may be administered once or several times during the period of administration of the therapeutic drug. During a period of combined administration of the active ingredient and the therapeutic drug, there may be a variety of possible combined administration regimes, for example, daily administration of both; daily administration of the therapeutic drug and several times daily administration of the active ingredient; a repeated cycle of administration comprising administering the therapeutic drug on one day and then the active ingredient on another day; etc.

According to an embodiment of the invention, the said active ingredient may be combined into a single composition with the other drug, and such a combined composition also forms an aspect of the invention.

The invention will now be illustrated in a non-limiting manner, by the following examples with occasional reference to the annexed drawings.

DETAILED DESCRIPTION OF THE INVENTION

EXAMPLE 1

In Vitro Studies

Material and Methods a. Tumor Cells

Tumor cell lines from human (K562 myeloid leukemia, Tib-180 erythroleukemia, LNCaP prostate carcinoma and MDA-MB468 breast adenocarcinoma), and murine (Yac lymphoma, B-16 melanoma) were used and were purchased from the American Type Tissue Culture Collection, Rockville. Nb2 11c rat lymphoma cells (Pines et al.[19], were also used. The cells were routinely maintained in RPM medium containing 10% fetal calf serum. Twice a week the cells were transferred to a freshly prepared medium.

Normal Cells

As a control for tumor proliferating cells, two normal proliferating cell types were used i.e., bone marrow cells derived from the femur of C57BL/6J mice; fibroblasts derived from primary cultures of newborn rat skeletal muscle cells. The cells were prepared as previously, (Djaldetti, M., Sredni, B., Zigelman, R., Verber, M., and Fishman, P. Muscle cells produce a low molecular weight factor with anti-cancer activity. *Clin. Exp. Matastasis*, 14:189–196, 1996). Also used was the L-8 myoblast rat cell line which was purchased from the ATCC.

c. Cell Proliferation Assays (i) Cell Count Assay:

The effect of adenosine on the proliferation of rat Nb2-11C lymphoma cells was monitored by cell counting. The Nb2-11C cells were synchronized in the GO/G1 phase prior to cultivation with the CM by transferring the cells to horse serum (Biological Industries, Beit Haemek, Israel) supplemented medium for overnight incubation. $1.2 \times 10^5$ cells/ml were cultured in 24 well plates in 1 ml RPMI medium containing 5% horse serum and 20, 10, 8, 6, 4, 2 and 1 $\mu$M of adenosine of adenosine (purchased from Sigma, USA) were added. Cell proliferation was initiated by the addition of Human Growth Hormone (Biotechnology General, Rehovot, Israel) to a final concentration of 2 ng/ml. The cultures were incubated at 37° C. at 5% $CO_2$ and counted in Coulter Counter 48 hours later. Inhibition of cell proliferation was calculated as follows:

$$I = \frac{C_s - C_{nh}}{C_{wh} - C_{nh}}$$

wherein I=degree of inhibition (%)

$C_s$=cell count with adenosine $C_{nh}$=cell count without hormone and without adenosine $C_{w/h}$=cell count with hormone but without adenosine.

(ii) [³]-Thymidine Incorporation Assay:

0.9×10⁴/well of each tumor cell line or normal cells (bone marrow cells or fibroblasts) were incubated with RPMI medium containing 10% FCS and 2 μM adenosine in 96 microtiter plates for 48 hours. During the last 6 hours of incubation, each well was pulsed with 1 μCi[³H]-Thymidine. The cells were harvested and the [³H]-Thymidine uptake was determined in an LKB liquid scintillation counter (LKB, Piscataway, N.J., USA).

Results a. Effect of Adenosine on Tumor and Normal Cell Proliferation

Figure 1:
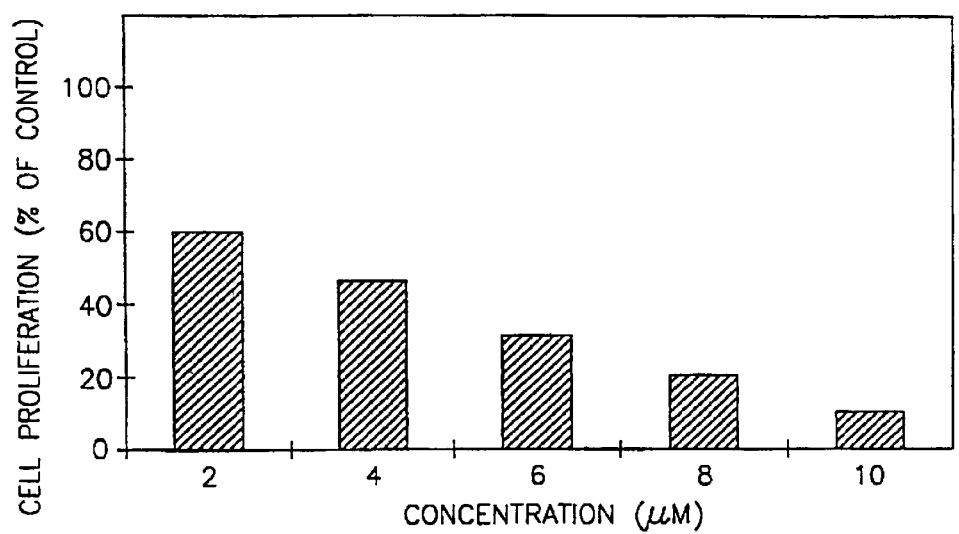
FIG. 1 shows the effect of increasing adenosine concentrations on the proliferation of Nb2-11c lymphoma cells, measured by cell count and expressed as percent of control.

The growth of the Nb2-11c rat lymphoma cells (measured by cell count) was markedly inhibited following incubation with different concentrations of adenosine. As can be seen in FIG. 1, there is a dose dependent effect of adenosine on the proliferation of the Nb2-11c cells.

Figure 2A:
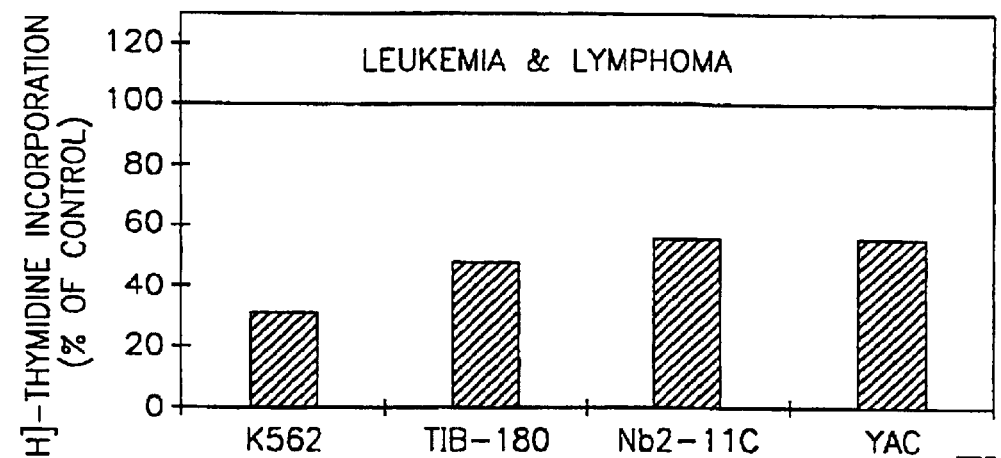
FIG. 2 shows the effect of 4 $\mu$M of adenosine on the proliferation of tumor and normal cells: Panel A shows the effect of adenosine on a number of leukemia and lymphoma cell lines; Panel B shows the effect of adenosine on a number of solid tumors; and Panel C shows the effect of adenosine on normal cells. Proliferation of cells was measured by a thymidine incorporation assay.
Figure 2B:
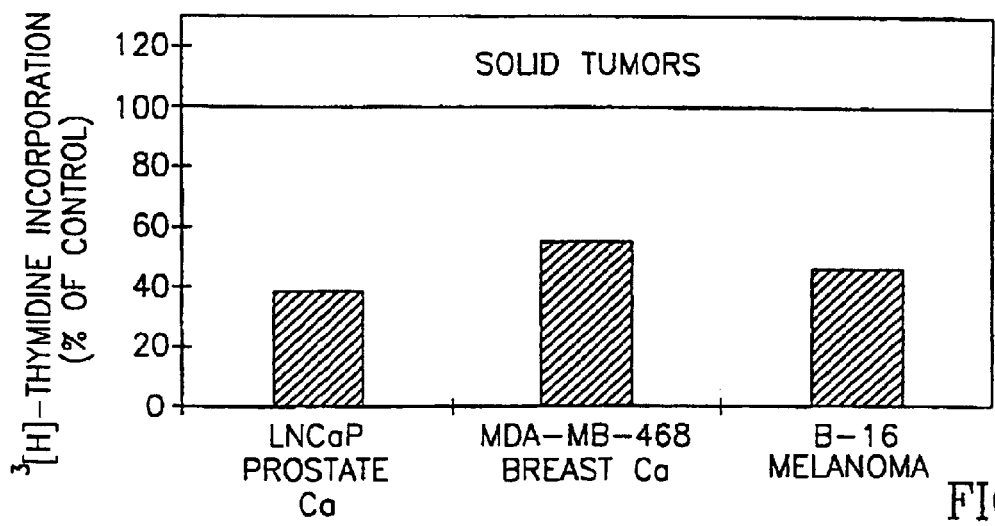
Figure 2C:
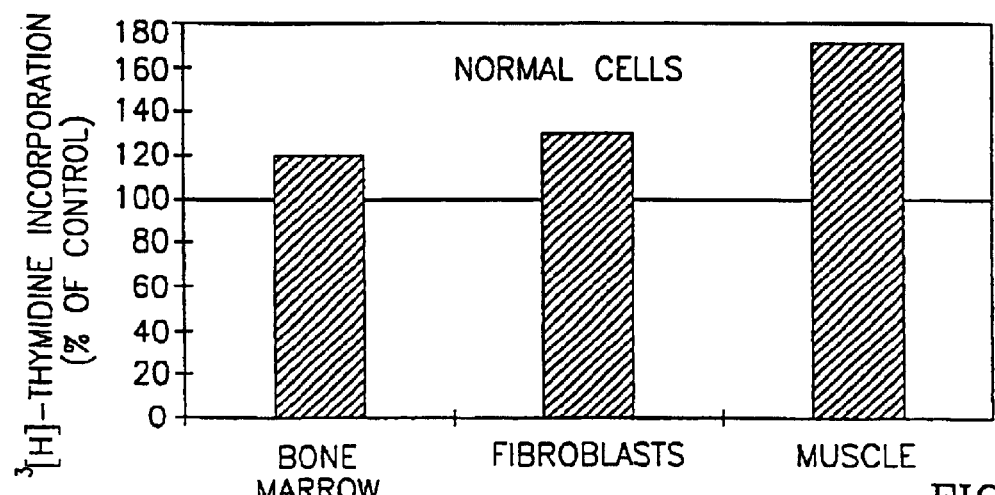
Figure 3:
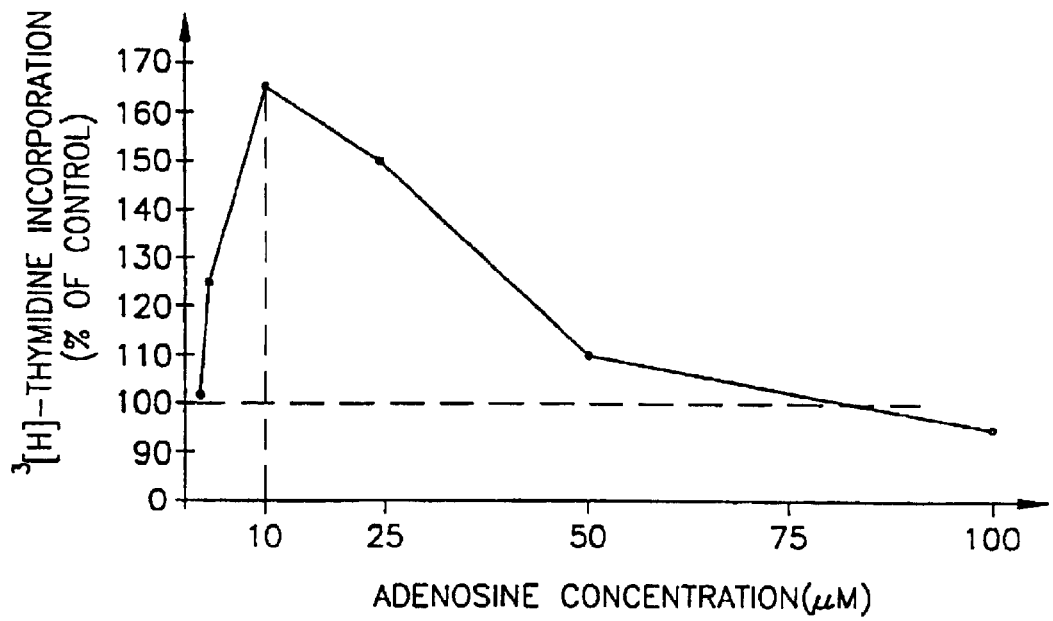
FIG. 3 shows the effect of different doses of adenosine on proliferation of bone marrow cells (measured by a thymidine incorporation assay).
Figure 4:
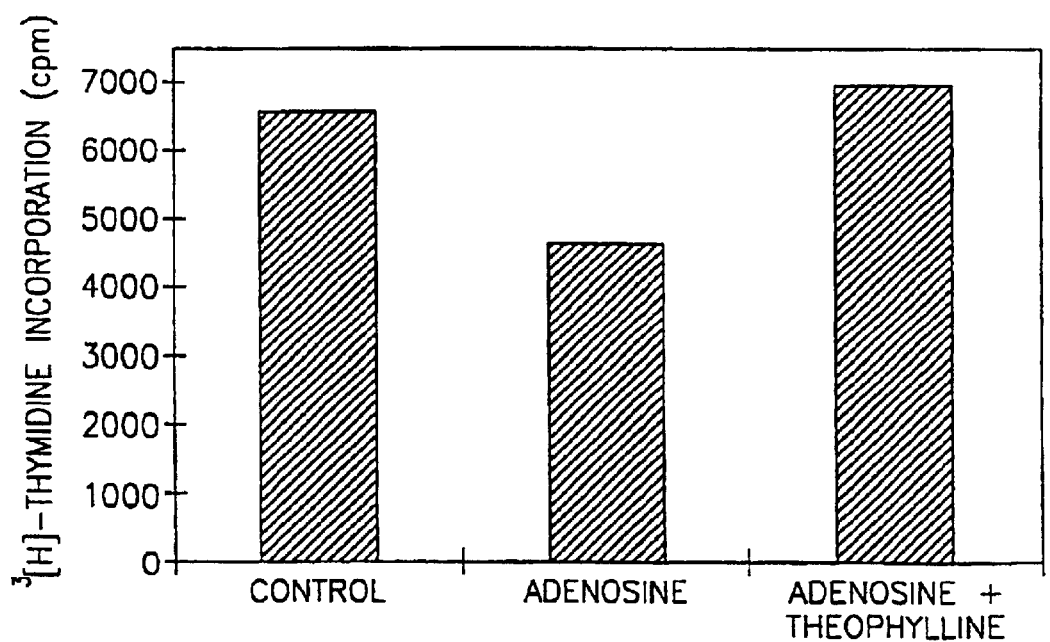
FIG. 4 shows the effect of theophylline in neutralizing the inhibitory effect of adenosine on tumor cell proliferation.

Adenosine in a concentration of 4 μM induced proliferation inhibition in the leukemia, lymphoma and the solid tumor cell lines, while in the same time it stimulated the proliferation of the three tested normal cells (FIG. 2): all results shown as % of control). Additional studies revealed a dose dependent stimulatory effect of adenosine on bone marrow cell proliferation (FIG. 3) with a peak activity at about 10 μM).

b. Theophylline (Adenosine A1&A2 Receptor Antagonist) Neutralizes the Inhibitory Effect of Adenosine on Tumor Cell Proliferation Theophylline is an antagonist of both A1 and A2 adenosine receptors. Theophylline in a concentration of 0.1 μM was added to a culture of K562 cells in the presence of 4 μM adenosine. Culture conditions were identical to those described above. As can be seen in FIG. 4, while adenosine inhibited tumor cell proliferation, in the presence of theophylline, this inhibitory effect was neutralized.

c. Effect of Theophylline (Adenosine A1 and A2 Receptor Antagonist). DPCPX (Adenosine A1 Receptor Antagonist) and DPSPX (Adenosine A2 Receptor Antagonist) on Bone Marrow Cell Proliferation Proliferation of bone marrow cells in the presence of the three adenosine receptor antagonists in the absence and in the presence of adenosine was tested. The concentration of Theophylline was 0.1 μM; and that of DPCPX and DPSPX was 0.01 μM. The concentration of adenosine was 10 μM.

Figure 5:
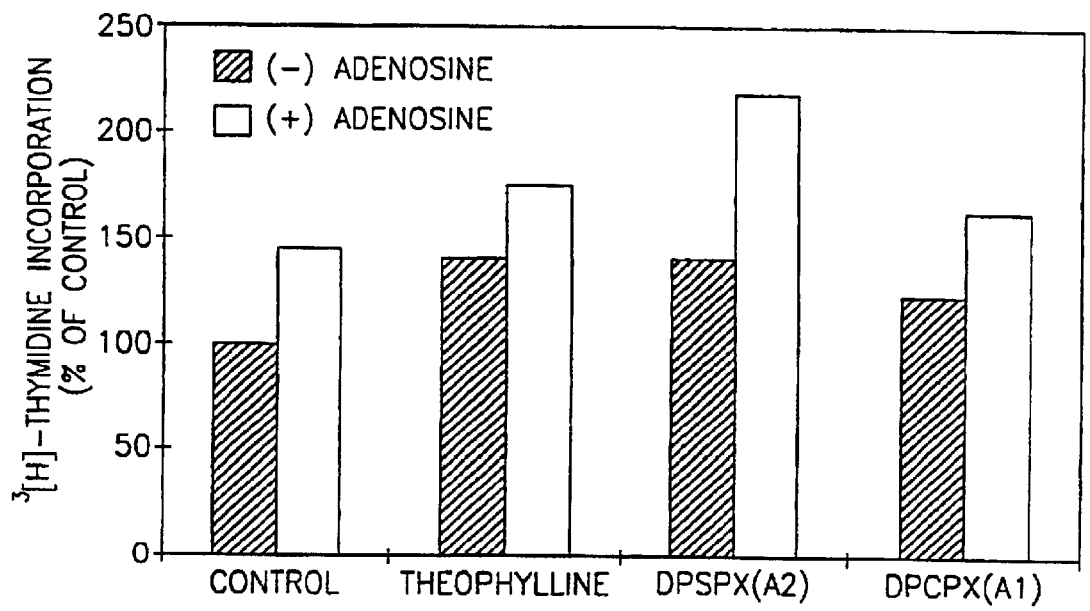
FIG. 5 shows the effect of adenosine receptor antagonists on proliferation of bone marrow cells (dark-colored columns show proliferation of bone marrow without adenosine; light-colored columns show the effect of proliferation in the presence of adenosine).

The results shown in FIG. 5 show that all these receptor antagonists caused a small increase in proliferation of bone marrow cells, while a much higher effect on increase of bone marrow cell proliferation was observed in the presence of adenosine. These results demonstrate that the stearatory effect of adenosine on bone marrow cells is likely through a mechanism not dependent on the adenosine receptors. In addition, although not wishing to be bound by theory, it is likely that the increase in proliferation obtained in the presence of the adenosine receptor antagonists is a result of freeing a larger amount of adenosine naturally present in the extracellular environment, e.g. adenosine secreted by cells from internal pools, to act through the proliferation stimulation pathways.

EXAMPLE 2

In Vivo Studies

Material and Methods

40 C57BL6/J mice were divided into 4 groups each of which were treated (by intraperitoneal injection) according to one of the following protocols:

1. control group: 6 days of treatment by daily injection of 1 ml saline.

2. adenosine and chemotherapy group: daily injection of a 1 ml 5 mM adenosine solution for 5 consecutive days. On day 6 the mice were injected intraperitoneally with cyclophosphamide.

3. adenosine group: daily injection of a 1 ml 5 nM adenosine solution for 5 consecutive days. On day 6 the mice were injected intraperitoneally with 1 ml saline.

4. chemotherapy group: daily injection of 1 ml saline for 5 consecutive days. On day 6 the mice were injected intraperitoneally with cyclophosphamide.

Five mice of each group were sacrificed 25 hrs and 96 hrs following the treatments and two parameters were evaluated:

1. complete blood cell count.

2. Proliferation capacity of bone marrow: bone marrow was aspirated from the femur and pooled for each tested group. The cells were separated, counted and the proliferative capacity was evaluated by the [³H]-Thymidine incorporation assay as described above.

Results

Adenosine has a Chemoprotective Effect

Following treatment with cyclophosphamide, the number of white blood cells dropped after 24 hrs as is shown in Table 1, below. In the group which was treated 5 days with adenosine prior to the cyclophosphamide administration, the number of white blood cells was even higher than that of the control group.

TABLE 1

| Group | WBC count × 10⁶/ml | |
|---|---|---|
| | 24 hours | 96 hours |
| control | 6.0 ± 0.75 | 6.0 ± 0.75 |
| adenosine | 9.37 ± 0.26 | 6.8 ± 0.73 |
| cyclophosphamide | 3.8 ± 0.18 | 3.62 ± 0.17 |
| adenosine + cyclophosphamide | 6.4 ± 0.58 | 7.32 ± 0.88 |

The protective effect of adenosine was also demonstrated when testing bone marrow cell proliferation, as can be seen in Table 2 below. It can be seen that adenosine increased the proliferating capacity of the bone marrow even above control, even in the presence of the chemotherapeutic drug.

TABLE 2

| | Bone Marrow Cell Proliferation (CPM) after 24 hours |
|---|---|
| Control | 603.6 ± 23.7 |
| Adenosine | 1480.0 ± 68.5 |
| Cyclophosphamide | 434.5 ± 52.2 |
| Adenosine + cyclophosphamide | 1072.6 ± 85.3 |

EXAMPLE 3

In Vivo Studies

Materials and Methods

40 C57BL6/J were divided into 4 groups, each of which was treated (by intraperitoneal injection) according to one of the following protocols:

1. Control group: 6 days of treatment by daily injection of 1 ml saline.

2. Chemotherapy group: daily injection of 1 ml saline for 5 consecutive days. On day 6 the mice were injected intraperitoneally with cyclophosphamide.

3. Adenosine group: daily injection of a 1 ml group 5 mM adenosine solution for 5 consecutive days. On day 6 the mice were injected intraperitoneally with 1 ml saline.

4. Adenosine and chemotherapy group: daily injection of a 1 ml 5 mM adenosine solution for 5 consecutive days.

The following parameters were evaluated for each group:
i. Red blood cell (RBC) count.
ii. Hemoglobin (HGB) level.
iii. White blood cell count.
iv. Proportion of the three major groups of white blood cells: Lymphocytes (LYM), Monocytes (MID) and Granulocytes (GRAN).

Results

The results (mean±S.E.) for each of the different groups is shown in the following Table 3.

TABLE 3

| Group | RBC[1] | HGB[2] | % LYM[4] | % MID[4] | % GRAN[4] |
|---|---|---|---|---|---|
| Control | 8.51 ± 0.17 | 14.06 ± 0.28 | 74.22 ± 3.36 | 10.46 ± 1.07 | 15.10 ± 2.72 |
| CHEMO | 8.65 ± 0.18 | 14.88 ± 8.32 | 81.94 ± 2.49 | 7.78 ± 0.92 | 10.28 ± 1.59 |
| AD(w) | 8.44 ± 0.16 | 14.03 ± 0.20 | 65.57 ± 3.35 | 13.4 ± 0.70 | 21.03 ± 2.75 |
| AD(w) + CH | 8.17 ± 0.28 | 13.06 ± 0.46 | 75.1 ± 3.89 | 9.00 ± 0.86 | 15.84 ± 3.08 |

[1]Red blood cell counts - $10^6$/l
[2]Hemoglobin count - in gram/100 ml
[3]% out of the number of white blood cells The above results demonstrate that while the chemotherapeutic drug had almost no effect on the red blood cell count and on the level of hemoglobin, it caused a reduction in the amount of white blood cells. As can be seen, the white blood cell count was boosted to levels above control after administration of adenosine and when adenosine was administered together with the chemotherapeutic drug, the white blood cell count remained at levels similar to control.

The above results demonstrate that while the chemotherapeutic drug had almost no effect on the red blood cell count and on the level of hemoglobin, it caused a reduction in the amount of white blood cells. As can be seen, the white blood cell count was boosted to levels above control after administration of adenosine and when adenosine was administered together with the chemotherapeutic drug, the white blood cell count remained at levels similar to control.

While the chemotherapeutic drugs have a toxic effect and thus give rise to reduction in count of all white blood cells, this effect is more dominant on granulocytes. This can be seen by the fact that following administration of the chemotherapeutic drug the relative proportion of granulocytes decreases while the relative proportion of lymphocytes decreases. This effect is reversed upon administration of adenosine, namely, adenosine has a more pronounced effect in causing proliferation of granulocytes in various other types of white blood cells.

EXAMPLE 3

Additional In Vivo Studies

In a large number of in vivo studies conducted using similar protocols, the adenosine dosage which was used was reduced to about 54 µ/kg body weight per day, with a similar effect of adenosine, in toxic effect of the chemotherapeutic drag on the count of leukocytes and peripheral blood granulocytes. Additionally, in further experiments conducted in accordance with the invention it was found that in order to exert its protective effect, it is sufficient to administer the adenosine for several days prior to the treatment with the chemotherapeutic drug and this effect does not require continued administration of adenosine during the course of treatment with a chemotherapeutic drug.

EXAMPLE 4

In Vivo Studies

Materials and Methods

B-16-F10 melanoma cells ($2\times10^5$) were intravenously injected to 40 C57BL6/J mice. The mice were divided into 4 groups each of 10 mice which were treated by intraperitoneal administration of one of the following:

1. Control group: daily administration of 1 ml saline, per mouse from day of tumor inoculation until the mice were sacrificed.
2. Adenosine group: daily administration of 1 ml of a 5 mM adenosine solution per mouse from day of tumor inoculation until the mice were sacrificed.
3. Chemotherapy group: one injection of cyclophosphamide 24 hrs after inoculation of tumor cells and daily administration of 1 ml of saline per mouse from day of tumor inoculation until the mice were sacrificed.
4. Chemotherapy and adenosine: one injection of cyclophosphamide 24 hrs after inoculation of tumor and daily administration of 1 ml of 5 mM per mouse from day of tumor inoculation until the mice were sacrificed.

Results

Following 18 days the mice were sacrificed and melanoma tumor foci were counted in the lung. The results are summarized in Table 4.

TABLE 4

| Group | No. of foci |
|---|---|
| control | 7.6 ± 2.68 |
| adenosine | 6.11 ± 2.74 |
| chemotherapy | 4.16 ± 1.42 |
| adenosine + chemotherapy | 3.0 ± 1.16 |

The above result demonstrates the adjunctive effect of adenosine in increasing potency of the anti-tumor effect of the chemotherapeutic drug.

Figure 6:
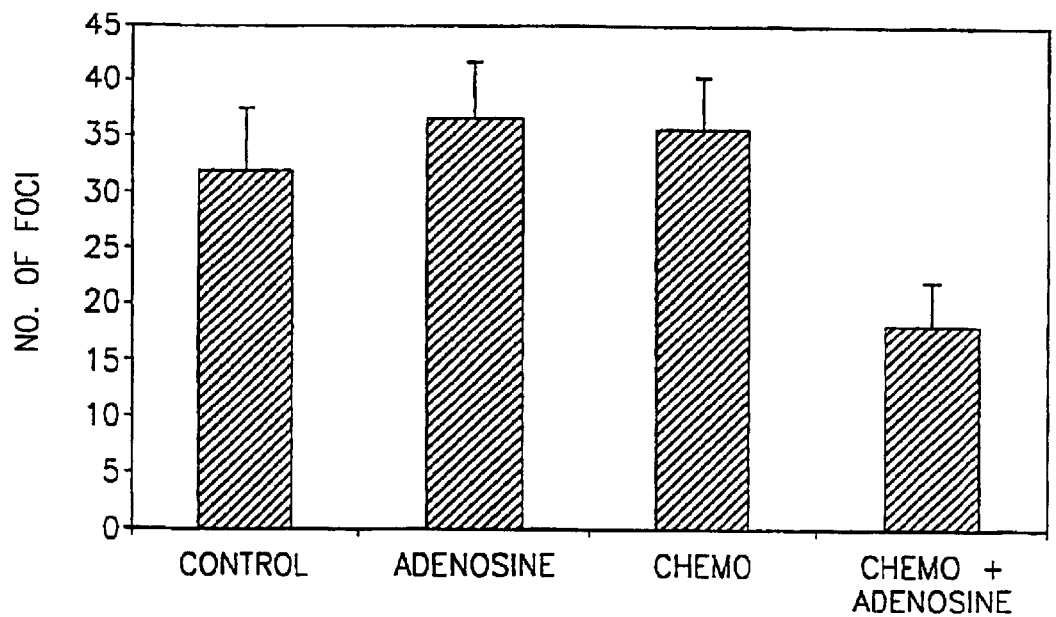
FIG. 6 shows the in vivo anti-tumor effect of three different treatments: administration of adenosine, administration of a chemotherapeutic drug—cyclophosphamide, and a combination of adenosine and the chemotherapeutic drug. The effect was measured by counting the number of tumor foci in the lungs of the tested mice.

In another experiment, a similar protocol was followed, with a lower dosage of adenosine (oral administration of 0.5 ml of a 10 µM adenosine solution, a dose equal to about 54 µg/kg body weight of adenosine). The results are shown in FIG. 6. As can be seen, here again, adenosine synergized with the chemotherapeutic drug to reduce the tumor load.

EXAMPLE 5

In Vivo Studies

Materials and Methods

50 C57BL6/J mice were divided into 5 groups of 10 mice each, which were treated by intraperitoneal injection with one of the following treatments:

1. Control group: 6 days of treatment by daily injection of 1 ml saline.
2. Adenosine group I: daily injection of 1 ml 5 M adenosine solution for 6 days (a dose of about 5 µM/kg body weight).

3. Adenosine group II: daily injection of 1 ml 10 M adenosine solution for 6 days (a dose of about 1.08 μg/kg body weight).
4. Chemotherapy group: daily injection of 1 ml saline for 5 consecutive days. On day 6 the mice were injected intraperitoneally with cyclophosphamide.
5. Adenosine and chemotherapy group: daily injection of 1 ml 10 M adenosine solution for 5 consecutive days. On day 6 the mice were injected intraperitoneally with cyclophosphamide.

Results

The total white blood cell count and the percentage of granulocytes, in each of the groups, is shown in the following Table 5.

TABLE 5

| Group | WBC (count × 10³/l) | GRAN (%) |
| --- | --- | --- |
| Control | 7.85 | 8.70 |
| 5 μM adenosine | 9.50 | 9.00 |
| 10 μM adenosine | 7.56 | 10.76 |
| Chemotherapy | 5.00 | 7.70 |
| 10 μM adenosine + chemotherapy | 6.35 | 11.41 |

The above results show that adenosine at both concentrations had no effect in increasing the percentage of granulocytes in the white blood cell population. In addition, while the chemotherapy caused a decreased in the number of white blood cells and in the relative proportion of granulocytes, the adenosine was capable of restoring the total white blood cell count, although not to full control levels, but more importantly, notwithstanding the chemotherapy, it yielded a very large increase in the relative proportion of granulocytes.

EXAMPLE 6

Adenosine Exerts an Immunomodulator Effect a. In Vivo Effect on NK Activity and IL-12 Secretion Mononuclear cells (MNC) were fractionated from heparinized blood of 10 healthy volunteers using Ficoll-Hypaque gradient. $5 \times 10^6$ mononuclear cells/ml were incubated with 4 μM adenosine and RPMI containing 10% FCS with and without 0.0075% of the mitogen Staphylococcus aureus Cowan I (SAC, Calbiochem Pansorbin) for 18 hours. At the end of the incubation period the supernatant was collected, centrifuged and filtered through 0.22μ sterile filter and kept at −70° C. until assayed. The level of IL-12 in the supernatants was analyzed using a commercial kit of R&D System.

The effect of adenosine on the activity of human peripheral blood NK cells was assayed by a standard 4 h $^{51}$Cr-release assay using K562 leukemia cells as targets. Peripheral blood mononuclear cells were separated from 10 healthy volunteers using Ficoll-Hypaque gradient. Cells were cultured at a concentration of $5 \times 10^5$ cells/well in 96 well round bottom plates, and used as the effector (E) cells. The cells were preincubated with 4 μM adenosine in RPMI containing 5% FCS for 18 hours. K562 cells were used as the targets (T) and were labeled with 100 μCi of $Na_2[^{51}Cr]O_4$ at 37° for 1 h. After extensive washing to remove the excess Cr, cells ($1 \times 10^4$) were resuspended and mixed with the effector cells at the E:T ratio of 1:50 in a volume of 200 μl using triplicate assays. After 4 h of incubation at 37° C. in 5% $CO_2$, plates were centrifuged, and the supernatants were counted in a gamma counter (LKB).

NK cytotoxicity was calculated using the following equation:

$$\% \text{ lysis} = \frac{cpm \text{ experiment} - cpm \text{ spontaneous}}{cpm \text{ maximal} - cpm \text{ spontaneous}} \times 10$$

where cpm spontaneous and cpm maximal were determined by measuring cpm of the supernatants of the target cells alone in the presence of assay medium or in the presence of 1% SDS, respectively. Spontaneous release was below 8% of the maximal release throughout this experiment.

Figure 7:
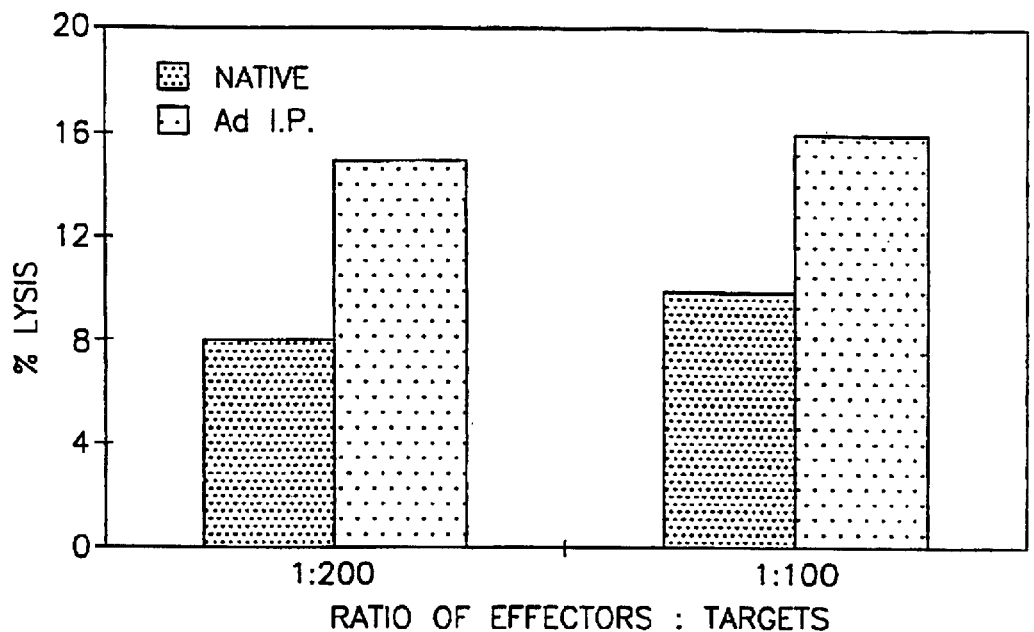
FIG. 7 shows the in vitro effect of adenosine on activity of human natural killer (NK) cells and IL-2 production by human peripheral monunuclear cells. (Control—dark columns; cells exposed to adenosine—light colored columns).

Results:

Adenosine stimulated the production of IL-12 by human peripheral blood mononuclear cells in the presence of SAC mitogen (FIG. 7). In another set of experiments adenosine induced IL-12 production without the presence of mitogen in the culture system (19% stimulation of IL-12 production). NK activity was also stimulated by 32% following the addition of adenosine to the culture system. It may be concluded that one of the potential mechanisms through which adenosine stimulates NK activity is the induction of IL-12 production which is known as an activator of NK cells.

b. In Vivo Effect of Adenosine on NK Activity of Mice Splenocytes

ICR mice were treated for 5 consecutive days with 10 μM of adenosine. Three days later the mice were sacrificed, spleens were taken out and mononuclear cells were separated using Ficoll Hypaque gradient. NK activity was measured as describe above for the human assay excluding the use of Yac murine lymphoma cells as targets instead of the K562 cells.

Figure 8:
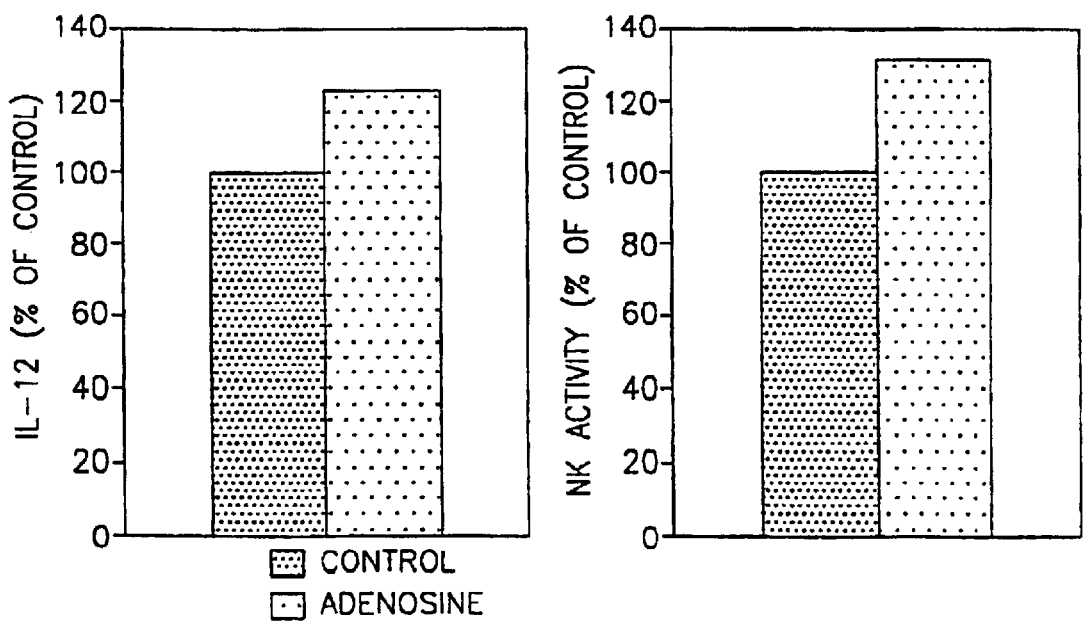
FIG. 8 shows the effect of in vivo administered adenosine on activity of NK cells. (Dark-colored columns—NK cells obtained from naive mice; light-colored columns—NK cells obtained from adenosine-treated mice).

Results:

NK cells derived from adenosine treated mice were more potent in lysing the Yac target cells as was seen in the two ratios of effectors:targets assayed (FIG. 8).

The modulating affect of adenosine may explaine some of its in vivo anti-tumoral activity shown below.

What is claimed is:

1. A method of treating or preventing drug-induced leukopenia in an individual, comprising administering to the individual an effective amount of adenosine, wherein said effective amount is no more than 10 mg/kg body weight.

2. A method according to claim 1, wherein said effective amount is no more than I mg/kg body weight.

3. The method of treating or preventing leukopenia in an individual according to claim 1, wherein said method is directed to treating leukopenia.

4. The method of treating or preventing leukopenia in an individual according to claim 1, wherein said method is directed to preventing leukopenia.

5. A method according to claim 1, wherein the drug is a chemotherapeutic drug.

6. A method according to claim 5, wherein said chemotherapeutic drug is an anti-cancer chemotherapeutic drug.

7. A method according to claim 6, comprising administering to the individual said effective amount of adenosine upon administration of said anti-cancer chemotherapeutic agent.

8. A method according to claim 7, wherein the amount of the chemotherapeutic drug is -lower than that used in the treatment of cancer involving administering said chemotherapeutic drug without said adenosine.

9. A method according to claim 5, wherein the drug is a chemotherapeutic drug.

10. A method for increasing the therapeutic index of a drug, said drug having toxic side effects manifested in leukopenia, the method comprising: administering to an individual treated with said drug an effective amount of adenosine for increasing the therapeutic index of a drug, said drug having toxic side effects manifested in leukopenia, said amount being no more than 10 mg/kg.

11. A method according to claim 10, wherein said therapeutic drug is an anticancer chemotherapeutic drug.

12. A method according to claim 10, wherein said effective amount is no more than 1 mg/kg body weight.

13. A method according to claim 10, wherein the increase in therapeutic index is manifested by:

increased efficacy of said therapeutic drug at the administered amount as compared to administration without adenosine;

reduced toxic side effects of said therapeutic drug; or increase in the duration-of-administration-of said therapeutic drug.

14. A method according to claim 13, wherein said therapeutic drug has a toxic side effect manifested in reduction of the level of leukocytes.

15. A method of increasing the white blood cell count in an individual, which comprises administering to said individual an effective amount of adenosine for increasing the white blood cell count in said individual, said amount being no more than 10 mg/kg body weight.

* * * * *